(12) United States Patent
Santhanagopalan et al.

(10) Patent No.: US 12,315,881 B2
(45) Date of Patent: May 27, 2025

(54) ELECTROLYTE COMPONENTS FOR CHARGING OF LITHIUM-ION BATTERIES

(71) Applicant: Alliance for Sustainable Energy, LLC, Golden, CO (US)

(72) Inventors: Shriram Santhanagopalan, Broomfield, CO (US); Ryan Ray Brow, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 641 days.

(21) Appl. No.: 17/704,145

(22) Filed: Mar. 25, 2022

(65) Prior Publication Data

US 2022/0311053 A1 Sep. 29, 2022

Related U.S. Application Data

(60) Provisional application No. 63/166,338, filed on Mar. 26, 2021.

(51) Int. Cl.
| | |
|---|---|
| *H01M 10/0567* | (2010.01) |
| *C07D 493/08* | (2006.01) |
| *H01M 10/0525* | (2010.01) |
| *H01M 10/0568* | (2010.01) |
| *H01M 10/0569* | (2010.01) |

(52) U.S. Cl.
CPC ...... *H01M 10/0567* (2013.01); *C07D 493/08* (2013.01); *H01M 10/0525* (2013.01); *H01M 10/0568* (2013.01); *H01M 10/0569* (2013.01); *H01M 2300/0037* (2013.01)

(58) Field of Classification Search
CPC ........ H01M 10/0567; H01M 10/0525; H01M 10/0568; H01M 10/0569; H01M 2300/0037; C07D 493/08
See application file for complete search history.

(56) References Cited

U.S. PATENT DOCUMENTS

| | | |
|---|---|---|
| 9,178,198 B2 | 11/2015 | Yeou et al. |
| 9,218,915 B2 | 12/2015 | Zhang et al. |
| 9,564,638 B2 | 2/2017 | Uemura |
| 10,023,587 B2 | 7/2018 | Kovach et al. |
| 10,424,812 B2 | 9/2019 | Nakazawa et al. |

(Continued)

OTHER PUBLICATIONS

"Gering et al., Electrolyte Design Factors to Enable Fast-Charge and Mitigate Lithium Metal Disposition, Jun. 2, 2020, XCEL, 2020 DOE Vehicle Technologies Office Annual Merit Review" (Year: 2020).*

(Continued)

*Primary Examiner* — Milton I Cano
*Assistant Examiner* — Jesse J Efymow
(74) *Attorney, Agent, or Firm* — Alexandra M Hall

(57) ABSTRACT

The present disclosure includes bridged bicyclic compounds and other non-flat organic molecules that have the ability to solvate lithium salts in higher concentrations without significant changes to the electrolyte viscosity which assists in improving the fast charge capability of lithium-ion cells. Using non-flat polar molecules may enable higher solubility of the salts while minimizing viscosity changes to the electrolyte. In some embodiments, the fused bicyclic compound is 7-oxabicyclo[2.2.1]heptane-2-carbonitrile (BHCN).

13 Claims, 13 Drawing Sheets

(56) References Cited

U.S. PATENT DOCUMENTS

| | | | |
|---|---|---|---|
| 2005/0053843 A1 | 3/2005 | Takahashi | |
| 2007/0243471 A1 | 10/2007 | Takahashi | |
| 2008/0154043 A1* | 6/2008 | Spurr | C07D 493/08 |
| | | | 549/463 |
| 2019/0348714 A1* | 11/2019 | Yoshida | C07F 9/00 |

OTHER PUBLICATIONS

Bachman et al., "Inorganic Solid-State Electrolytes for Lithium Batteries: Mechanisms and Properties Governing Ion Conduction", Chemical Reviews, 2016, vol. 116, No. 1, pp. 140-162.

Buss et al., "Nonaqueous Polyelectrolyte Solutions as Liquid Electrolytes with High Lithium Ion Transference Number and Conductivity", ACS Energy Letters, Jan. 2017, vol. 2, No. 2, pp. 481-487.

Du et al., "Enabling fast charging of high energy density Li-ion cells with high lithium ion transport electrolytes", Electrochemistry Communications, Jun. 2019, vol. 103, pp. 109-113.

Hilbig et al., "Butyronitrile-Based Electrolytes for Fast Charging of Lithium-Ion Batteries", Energies, Jun. 2019, vol. 12, No. 2869, pp. 1-18.

Mallarapu et al., "Understanding extreme fast charge limitations in carbonate mixtures", Journal of Materials Chemistry A, 2021, vol. 9, No. 8, pp. 4858-4869.

Prélot et al., "Structural-Chemical Disorder of Manganese Dioxides: 1. Influence on Surface Properties at the Solid-Electrolyte Interface," Journal of Colloid Interface Science, Jan. 2003, vol. 257, No. 1, pp. 77-84.

Takamura et al., "Ionic Conductivity of Gd2GaSbO7—Gd2Zr2O7 Solid Solutions with Structural Disorder," Solid State Ionics, Oct. 2000, vol. 134, No. 1-2, pp. 67-73.

Tuller, "Defect Engineering: Design Tools for Solid State Electrochemical Devices," Electrochimica Acta, Sep. 2003, vol. 48, Nos. 20-22, pp. 2879-2887.

Xu, "Electrolytes and Interphases in Li-Ion Batteries and Beyond", Chemical Reviews, Oct. 2014, vol. 114, No. 23, pp. 11503-11618.

Yang et al., "Fast charging of lithium-ion batteries at all temperatures", PNAS, Jun. 2018, vol. 115, No. 28, pp. 7266-7271.

Zhang et al., "Molecular Engineering toward Stabilized Interface: An Electrolyte Additive for High-Performance Li-Ion Battery", Journal of The Electrochemical Society, Oct. 2014, vol. 161, No. 14, pp. A2262-A2267.

Zheng et al., "Enhanced Li+ Ion Transport in LiNi0.5Mn1.5O4 through Control of Site Disorder", Physical Chemistry Chemical Physics, 2012, vol. 14, pp. 13515-13521.

Zheng et al., "Electrolyte additive enabled fast charging and stable cycling lithium metal batteries", Nature Energy, Mar. 2017, vol. 2, Article No. 17012, pp. 1-8.

International Search Report and Written Opinion for International (PCT) Application No. PCT/US2022/021848, Date of Mailing—Jun. 29, 2022, pp. 1-9.

Gering et al., "Electrolyte Design Factors to Enable Fast-Charge and Mitigate Lithium Metal Deposition", 2020 DOE Vehicle Technologies Office Annual Merit Review, Jun. 2020, Project ID: BAT471, Washington D.C., pp. 1-24.

* cited by examiner

ELECTROLYTE COMPONENTS FOR CHARGING OF LITHIUM-ION BATTERIES

CROSS-REFERENCE TO RELATED APPLICATIONS

This application claims priority to U.S. Provisional Patent Application No. 63/166,338 filed on Mar. 26, 2021, the contents of which are incorporated herein by reference in their entirety.

CONTRACTUAL ORIGIN

This invention was made with government support under Contract No. DE-AC36-08GO28308 awarded by the United States Department of Energy. The government has certain rights in this invention.

BACKGROUND

Lithium-ion batteries are rechargeable, enabling them to be used (i.e., discharged) and reused (i.e., charged then discharged again) multiple times. Lithium ions move from the anode (i.e., negative electrode) through an electrolyte to the cathode (i.e., positive cathode) during discharge (i.e., when the battery is being used to power a device). During charging, lithium-ions move from the cathode, through the electrolyte solution, to the anode. Charging generally requires an external power source to provide a voltage higher than that of the lithium-ion battery, to force a current to flow in the cell, spurring the lithium ions to begin moving. Charging may include the external power source applying a constant current, a constant voltage, or a combination of the two in different phases.

Proper procedures must be followed when charging lithium-ion batteries, as improper charging can damage or even destroy the battery. Most consumer-orientated lithium-ion batteries charge to a voltage of approximately 4.2 V per cell with a tolerance of approximately ±50 mV. Charging of lithium-ion batteries can take anywhere from about 30 minutes to about 50 hours, depending on the application or battery cell format, among other things. Typical consumer-oriented batteries often take about 3-10 hours. Therefore, there remains a need to reduce the time it takes to charge lithium-ion batteries.

SUMMARY

An aspect of the present disclosure is a composition of an electrolyte solution for a lithium-ion battery, the composition including a fused bicyclic compound including an oxygen group in a cross bridge, and a halide group. In some embodiments, the fused bicyclic compound is 7-oxabicyclo[2.2.1]heptane-2-carbonitrile (BHCN). In some embodiments, the electrolyte solution also includes a salt. In some embodiments, the salt comprises at least one of lithium tetrafluoroborate (LiBF$_4$), lithium bis(trifluoromethanesulfonyl)imide (LiTFSI), lithium bis(oxalato)borate (LiBOB), lithium oxalyldifluoroborate (LiODFB), lithium fluoroalkylphosphate, lithium 4,5-dicycano-2-(trifluoromethyl) imidazolide (LiTDI), or lithium hexafluorophosphate (LiPF$_6$). In some embodiments, the salt has a concentration in the range of about 0.01 M to about 4.2 M. In some embodiments, the lithium-ion battery has an increased cell capacity (mAh/g) over a typical lithium-ion battery containing 1.2M LiPF$_6$ in a combination of solvents (e.g., EC: EMC in the ratio 3:7) when the charging time to 4.2V is less than about 12 minutes. In some embodiments, the increased cell capacity is at least 10%. when subjected to charging at currents of less than about 5 C in less than about 12 minutes for voltages less than about 4.2 V. In some embodiments, the lithium-ion battery can be charged from 1 to 100% state of charge in less than about 12 minutes.

An aspect of the present disclosure is a lithium-ion battery including an anode, a cathode, and an electrolyte solution, in which the electrolyte solution includes a fused bicyclic compound including an oxygen group in a cross bridge, and a halide group. In some embodiments, the fused bicyclic compound is 7-oxabicyclo[2.2.1]heptane-2-carbonitrile (BHCN). In some embodiments, the lithium-ion battery has an increased cell capacity (mAh/g) over a typical lithium-ion battery containing 1.2M LiPF$_6$ in a combination of solvents (e.g., EC: EMC in the ratio 3:7) when the charging time to 4.2V is less than about 12 minutes. In some embodiments, the increased cell capacity is at least 10%. when subjected to charging at currents of less than about 5 C in less than about 12 minutes for voltages less than about 4.2 V. In some embodiments, the lithium-ion battery can be charged from 1 to 100% state of charge in less than about 12 minutes.

An aspect of the present disclosure is a method for improving the performance of a lithium-ion battery, the method including a fused bicyclic compound in an electrolyte solution; in which the lithium-ion battery includes an anode, a cathode, and the electrolyte solution, and the fused bicyclic compound includes an oxygen group in a cross bridge, and a halide group. In some embodiments, the fused bicyclic compound is 7-oxabicyclo[2.2.1]heptane-2-carbonitrile (BHCN). In some embodiments, the lithium-ion battery has an increased cell capacity (mAh/g) over a typical lithium-ion battery containing 1.2M LiPF$_6$ in a combination of solvents (e.g., EC: EMC in the ratio 3:7) when the charging time to 4.2V is less than about 12 minutes. In some embodiments, the increased cell capacity is at least 10%. when subjected to charging at currents of less than about 5 C in less than about 12 minutes for voltages less than about 4.2 V. In some embodiments, the lithium-ion battery can be charged from 1 to 100% state of charge in less than about 12 minutes.

BRIEF DESCRIPTION OF DRAWINGS

Some embodiments are illustrated in referenced figures of the drawings. It is intended that the embodiments and figures disclosed herein are considered illustrative rather than limiting.

DETAILED DESCRIPTION

Figure 1:
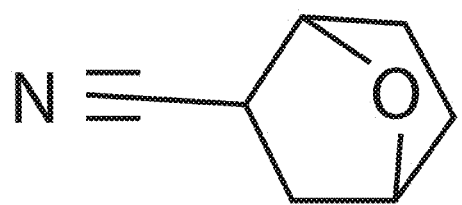
FIG. 1 illustrates the chemical structure of 7-oxabicyclo[2.2.1]heptane-2-carbonitrile (BHCN), according to some aspects of the present disclosure.

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

Among other things, the present disclosure relates to compounds included in the electrolyte solution of lithium-ion batteries, which maybe enable improved charging times for the lithium-ion battery by increasing the number of lithium-ion carriers available within the electrolyte solution. The electrolyte solution may include a fused bicyclic compound having an oxygen group in a cross bridge and a halide group. In some embodiments, the electrolyte solution may include 7-oxabicyclo[2.2.1]heptane-2-carbonitrile (BHCN).

The present disclosure includes bridged bicyclic compounds and other non-flat organic molecules that can solvate lithium salts in higher concentrations without significant changes to the electrolyte viscosity which assists in improving the fast charge capability of lithium-ion cells. The bridged bicyclic compounds may enable the dielectric constant of the electrolyte across a wide range of temperatures at high salt concentrations, relying upon the steric properties of the solvent molecules. Using non-flat polar molecules may enable higher solubility of the salts while minimizing viscosity changes to the electrolyte. Certain embodiments of the present disclosure may be agnostic to various salts present in the electrolyte solution. Examples of salts may be such as lithium hexafluorophosphate ($LiPF_6$), lithium bis (fluorosulfonyl) imide (LiFSI), and/or bis(trifluoromethanesulfonyl)imide (LiTFSI) which may deliver good cycle, higher transference number, and/or stability. The present disclosure includes improvements to the solvent composition and/or the solvation sheath that surrounds the salts.

Design of a functional electrolyte than can enable fast charging of lithium-ion batteries within 15 minutes or less requires an ionic conductivity of greater than 5 mS/cm, a bulk diffusivity of $1 \times 10^{-9}$ m$^2$/s or better, and a transport number higher than 0.75, based on calculations for a cathode loading of 4 mAh/cm$^2$. The current state-of-the-art Gen-2 electrolyte (ethylene carbonate (EC) and ethyl methyl carbonate (EMC) in a 3:7 ratio by weight, containing 1.2M $LiPF_6$) has been used very successfully over the last two decades because it overcomes limitations with the wide operating window (0-4.5V), reasonable operating temperatures (in the range of about 0 to about 60° C.) and delivers good cycling performance due to its ability to form a good barrier layer on the anode surface (known as the solid electrolyte interface or SEI). To deliver target properties listed above include limited solubility of lithium salts in the electrolyte, changes to properties like dielectric constant and viscosity (which in turn affect transport properties listed above) with salt concentration and/or temperature.

Some linear compounds (e.g., nitriles) have a high dielectric constant and a low viscosity—providing room for improving ionic conductivity to target values; however, lithium salts usually have poor solubility in these solvents. Limitations to solubility can be overcome using steric effects: for instance, the use of cyclic polyether compounds to promote the solvation of lithium salts in nonaqueous electrolytes is well documented. However, these compounds often suffer from limited oxidation stability at the cathode surface.

The use of fused bicyclic compounds alongside carbonates as solvents in lithium-ion batteries helps overcome several of these barriers. These compounds have several advantages relevant to improving fast charge performance of battery electrolytes: i) electrolytes with high dielectric constants are well known to improve transport; but with traditional polar molecules, the dipoles become "frozen" closer to the melting points and as a result, there is a reduction in transport properties. The bicyclic compounds retain their freedom of rotation at nominal operating temperatures for the battery, which are often well below their melting points ii) these compounds have higher solubilities due to their non-planar structure iii) steric hinderance prevents traditional issues associated with decomposition of cyclic carbonates (or polymerization of nitriles) enabling operation at high voltages.

FIG. 1 illustrates the chemical structure of 7-oxabicyclo[2.2.1]heptane-2-carbonitrile (BHCN), according to some aspects of the present disclosure. As shown in FIG. 1, BHCN is an exemplary fused bicyclic compound having an oxygen in a cross bridge of a benzene ring with a halide group attached to one carbon of the benzene ring. Other similar compounds having these features could be used as well.

Figure 2:
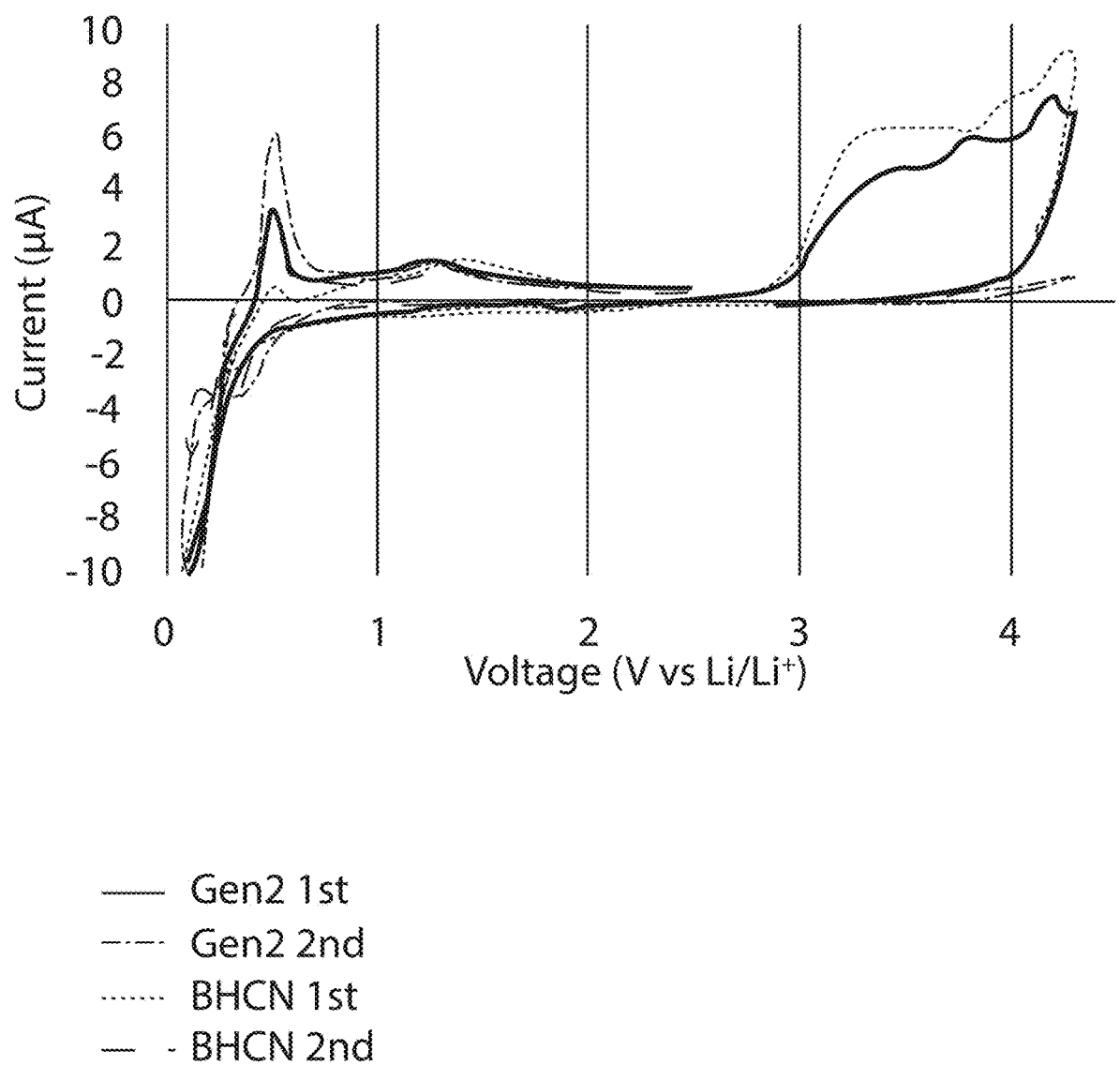
FIG. 2 illustrates the two experiments (using lithium metal electrodes and aluminum electrodes) with BHCN in the electrolyte solution compared to a standard electrolyte solution (referred to as "Gen2"), according to some aspects of the present disclosure.

Cyclic voltammetry was used to identify additional redox reactions that may be attributed to the addition of BHCN (10 wt %) to a standard electrolyte (referred to as "Gen2") of 1.2M lithium hexafluorophosphate (LiPF$_6$) in ethylene carbonate:ethylmethyl carbonate (EC:EMC) in a 3:7 ratio by weight solution. A u-shaped cell containing a lithium and aluminum electrode with unknown surface area was first submerged into the Gen2 electrolyte and cycled between 0.1 V and 4.3 V at a particular scan rate in an argon glove box (with a water concentration of less than 0.1 ppm). The experiment was then repeated with fresh electrodes and 10 wt % BHCN in Gen2. FIG. 2 illustrates these experiments. The aluminum oxidation peak occurs for both electrolyte solutions at the same voltage of 3.3 V for the first cycle, other oxidative peaks at 3.8 V and 4.1 V are shifted up in the electrolyte solution containing BHCN. No additional redox peaks occur in the electrolyte solution containing BHCN compared to the Gen2 electrolyte, suggesting that BHCN has a suitable electrochemical window for typical commercial lithium-ion battery chemistries.

Diffusion coefficients were determined using the steady state polarization method. Lithium metal electrodes with a glass filter (Whatman glass microfiber filters, grade GF/F with a thickness of 300 μm) underwent galvanostatic polarization until the cell potential reached a steady state. The current was then removed, and the cell potential was allowed to relax to equilibrium. Excess electrolyte of the Gen2 was mixed with varying concentrations of LiPF$_6$ (concentrations varied between 0.2 M and 4.0 M). BHCN was added to the same solvent concentration in either 10 or 20 weight percent. All electrolyte mixing occurred in an argon-filled glovebox with less than 0.1 ppm water (H$_2$O). Cells were polarized to reach an approximate steady-state potential near 100 mV before being allowed to relax for at least 24 hours before the next experiment began.

Figure 3:
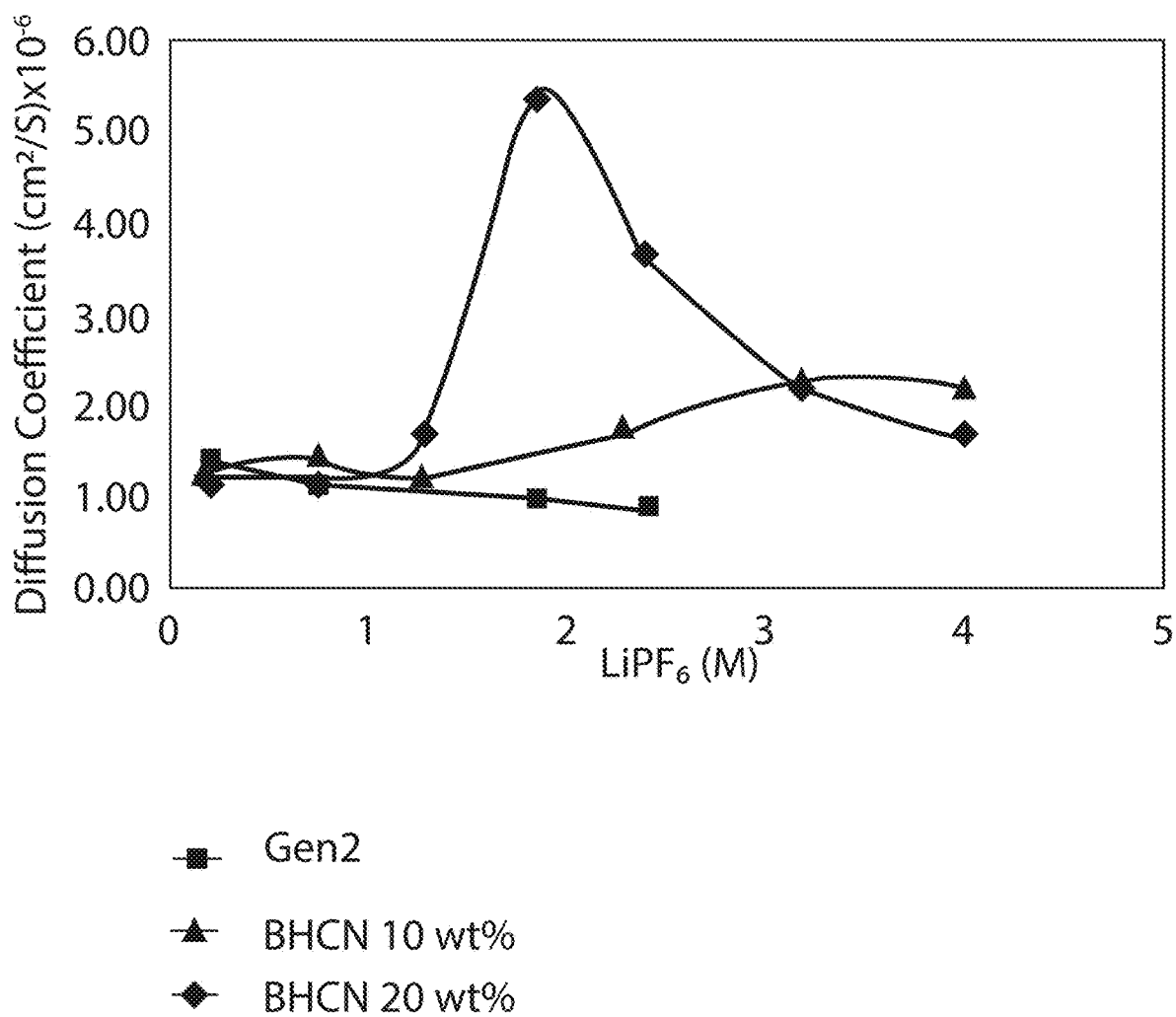
FIG. 3 illustrates diffusion coefficient compared to concentration of lithium hexafluorophosphate (LiPF$_6$) for an electrolyte solution containing BHCN 10 wt %, an electrolyte solution containing BHCN 20 wt %, and a Gen2 electrolyte solution, according to some aspects of the present disclosure.

Diffusion coefficients were calculated. FIG. 3 illustrates diffusion coefficient compared to concentration of lithium hexafluorophosphate (LiPF$_6$) for an electrolyte solution containing BHCN 10 wt %, an electrolyte solution containing BHCN 20 wt %, and a Gen2 electrolyte solution, according to some aspects of the present disclosure. Electrolyte solutions containing BHCN show higher diffusion coefficients at higher salt concentrations, suggesting BHCN plays a role in solvation. The diffusion coefficients could be calculated from the binary effective diffusion coefficient using:

$$D_{\pm,eff} = \epsilon \tau^{-1} D_{\pm}$$

Where $\epsilon$ is the porosity of the separator and $\tau$ is its tortuosity. The tortuosity of the separator may be calculated using the above equation. The Bruggeman coefficient for this separator was calculated as approximately 3.44. The effective binary diffusion coefficient was determined from the long-term relaxation behavior to ensure small changes in the salt concentration and the relationship is shown below $$D^*_{\pm,eff}(c_0) = \frac{l^2}{\pi^2} m_{ln}$$

Figure 4:
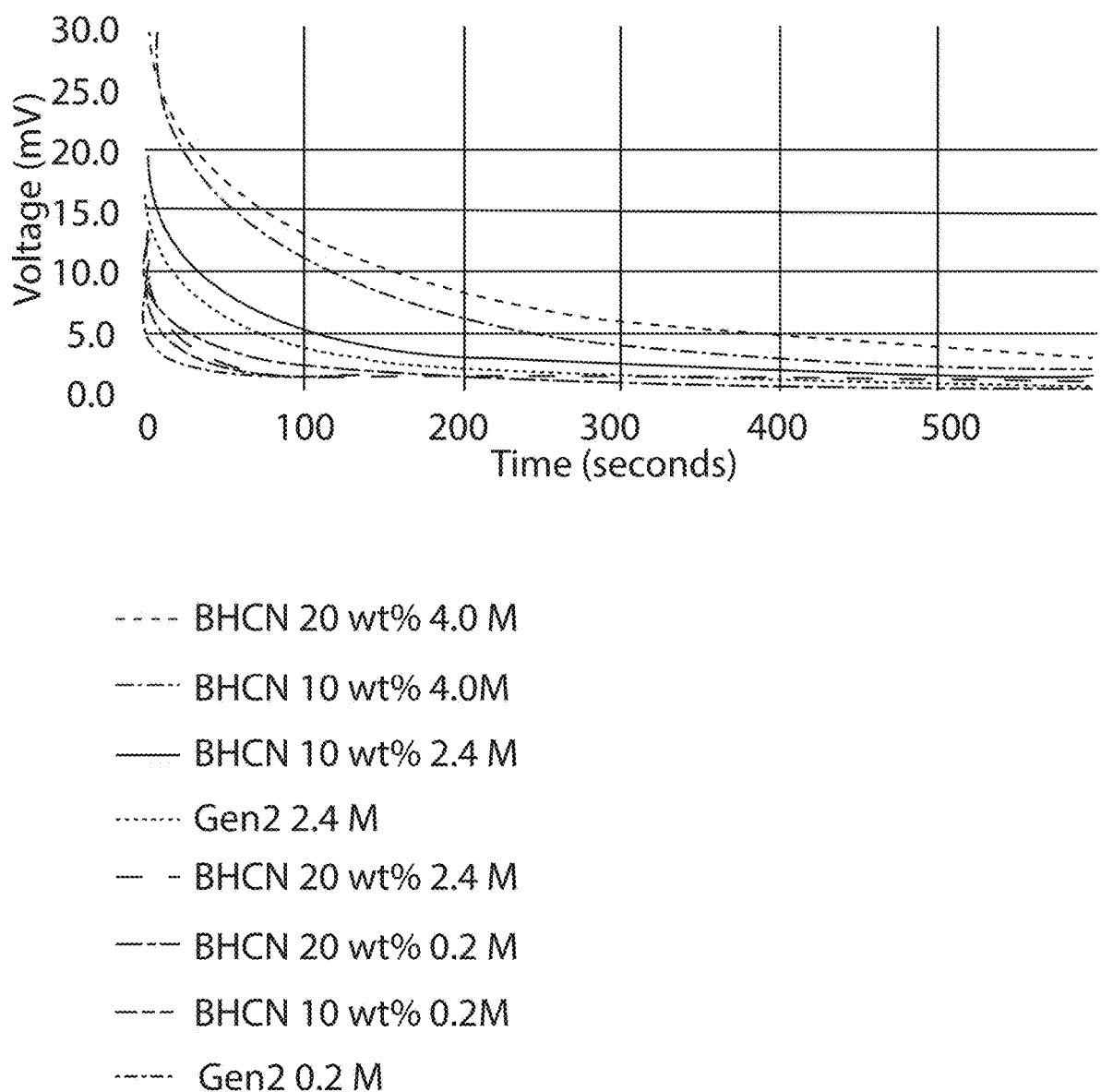
FIG. 4 illustrates a steady state polarization relaxation curve for electrolyte solutions containing BHCN at different wt % and two Gen2 electrolyte solutions, according to some aspects of the present disclosure

Here, l is the thickness of the separator (approximately 300 μm in this experiment) and $m_{ln}$ is the slope when ln(U) is plotted versus time as time approaches infinity. The separator is a permeable membrane positioned between the anode and cathode. The separator prevents electrical short circuits while allowing the transport of lithium ions between the two electrodes. FIG. 4 illustrates a steady state polarization relaxation curve for electrolyte solutions containing BHCN at different wt % and two Gen2 electrolyte solutions, according to some aspects of the present disclosure. An exponential decay in the cell potential can be seen in FIG. 4 as time increases. The time directly after the current is interrupted was excluded from the calculation. As seen in FIG. 4, that the additive does not contribute much in the way of the diffusion coefficient at the lower salt concentrations, it does result in an increase (when compared to the Gen2 electrolyte solution) in the diffusion coefficient at approximately 2.4 M LiPF$_6$ salt concentration witnessed by how quickly the cell potential decreases with time.

Figure 5:
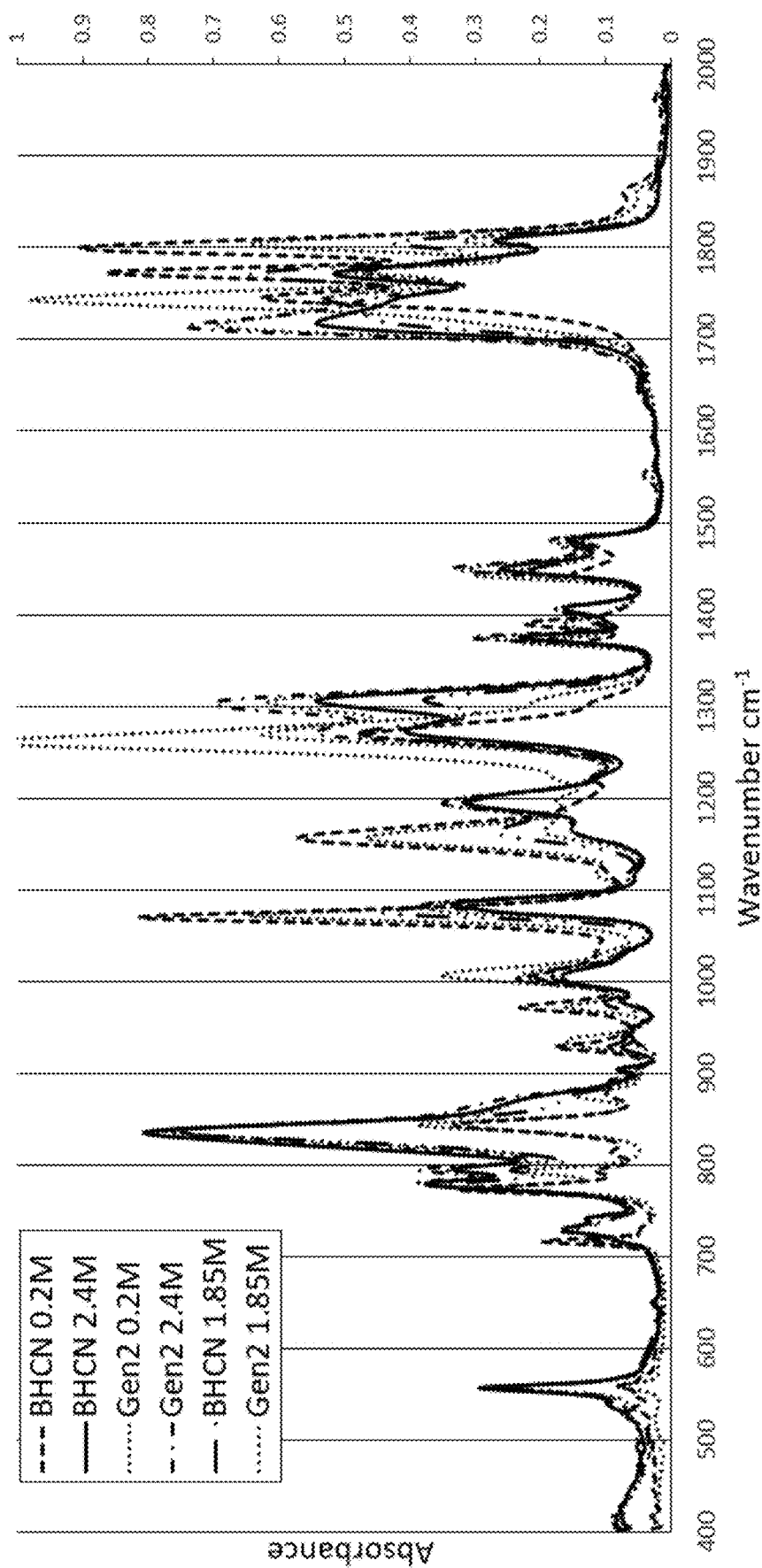
FIG. 5 illustrates Fourier transform infrared spectroscopy (FTIR) spectra of several Gen2 electrolyte solutions and electrolyte solutions containing BHCN, according to some aspects of the present disclosure.

FIG. 5 illustrates Fourier transform infrared spectroscopy (FTIR) spectra of several Gen2 electrolyte solutions and electrolyte solutions containing BHCN, according to some aspects of the present disclosure. FIG. 5 shows FTIR spectra of Gen2 electrolyte and an electrolyte solution containing approximately 20 wt % BHCN with varying salt concentrations (about 0.2 M, about 1.85 M, and about 2.4 M of LiPF$_6$). The lithium shifted modes show more absorbance with increasing LiPF$_6$ salt concentration for solutions containing BHCN suggesting that the nitrile groups are not yet saturated. Drops of the samples were placed on to a monolithic diamond ATR and scanned from about 400 to about 4000 cm$^{-1}$. Evidence that lithium (Li) ions are solvated by the BHCN is seen at the carbon-nitrogen triple bond with lithium ions in solution causes this peak to shift 28 cm$^{-1}$ (not shown in FIG. 5). Peak at about 1720 cm$^{-1}$ shows a lower-than-expected peak area and blue shift from the carbon-oxygen double bond stretching mode with suggests that BHCN has displaced some of the EC in lithium's solvation shell. In the solvation shell of the traditional Gen2 electrolyte, EC and EMC compete for lithium-ion coordination and EC is preferred when the electrolyte contains lower salt concentrations. EC solvation reaches saturation at some point, where EMC plays a larger role in solvation. Although it's difficult to interpret peaks at about 1770 and about 1800 cm-1 due to Fermi resonance, it is generally held that the peak located at about 1800 $cm^{-1}$ belongs to the uncoordinated carbon-oxygen double bond stretching mode of EC. The electrolyte solution containing BHCN shows more absorbance at this location. Two more peaks associated with EC, the methyl twist and the oxygen-carbon-oxygen stretch located near about 1170 $cm^{-1}$ and about 1080 $cm^{-1}$ respectively all suggest that EC has been displaced for lithium's solvation shell in all aspects. EC oxygen-carbon-oxygen stretch modes are shown with more uncoordinated EC for a given salt concentration compared with the Gen2 electrolytes, demonstrating the BHCN displaces EC in lithium's solvation shell.

As shown in FIG. 5, the anion phosphorous-fluorine absorption has been seen at about 844 $cm^{-1}$ but this peak splits once its symmetry has been disrupted in solution yielding a peak at about 834 $cm^{-1}$ and about 877 $cm^{-1}$. This suggests that the anions undergo a transition from majority solvent separated ions to majority contact ion pairs somewhere between about 1.0 M and about 2.0 M $LiPF_6$. At low salt concentrations, the uncoordinated phosphorous-fluorine peak located at about 845 $cm^{-1}$ is more intense for the Gen2 electrolyte, however, as the salt concentration is increased, electrolyte solutions containing BHCN show more uncoordinated phosphorous-fluorine anions at about 834 $cm^{-1}$ and less lithium coordinated phosphorous-fluorine at about 867 $cm^{-1}$. This may be caused by less BHCN participating in the lithium-ion solvation shell at lower salt concentrations, when anions are associated as solvent separated ions, but more BHCN participates to displace anions from forming contact pairs at higher salt concentrations.

Figure 6:
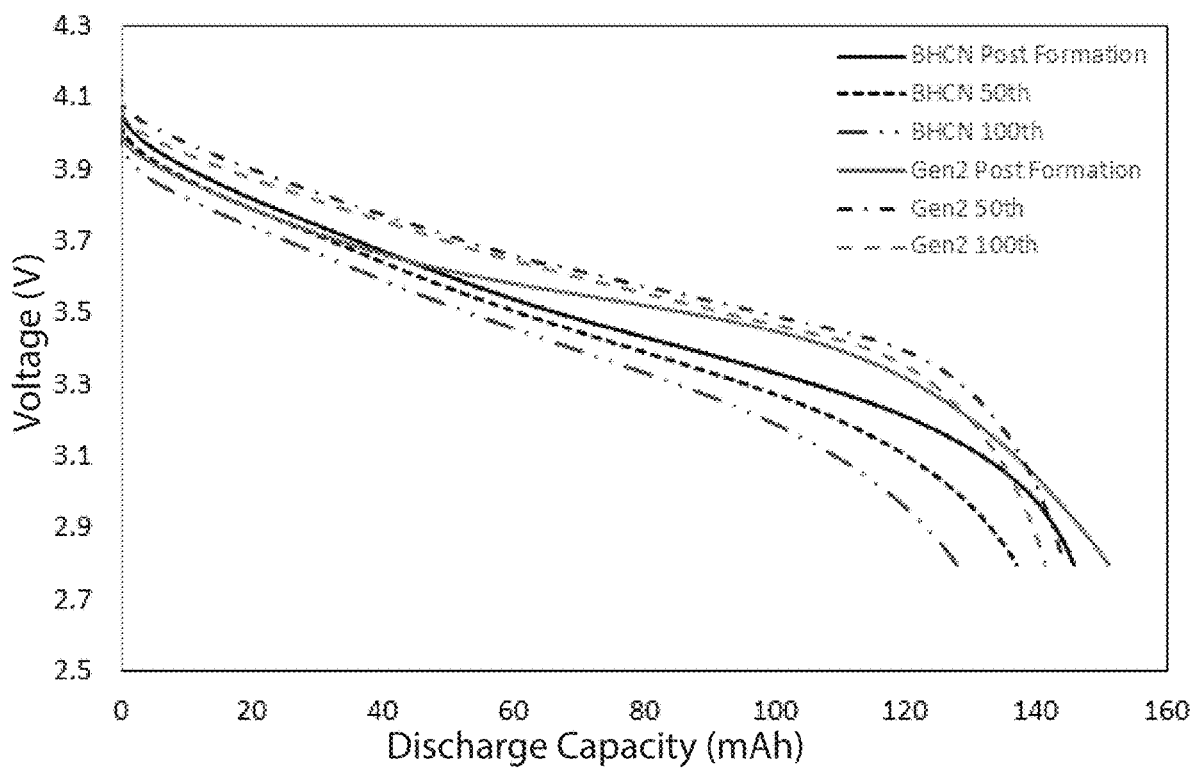
FIG. 6 illustrates data showing the discharge capacity compared to voltage for lithium-ion batteries with an electrolyte solution containing BHCN and lithium-ion batteries using a Gen2 electrolyte, according to some aspects of the present disclosure.
Figure 7:
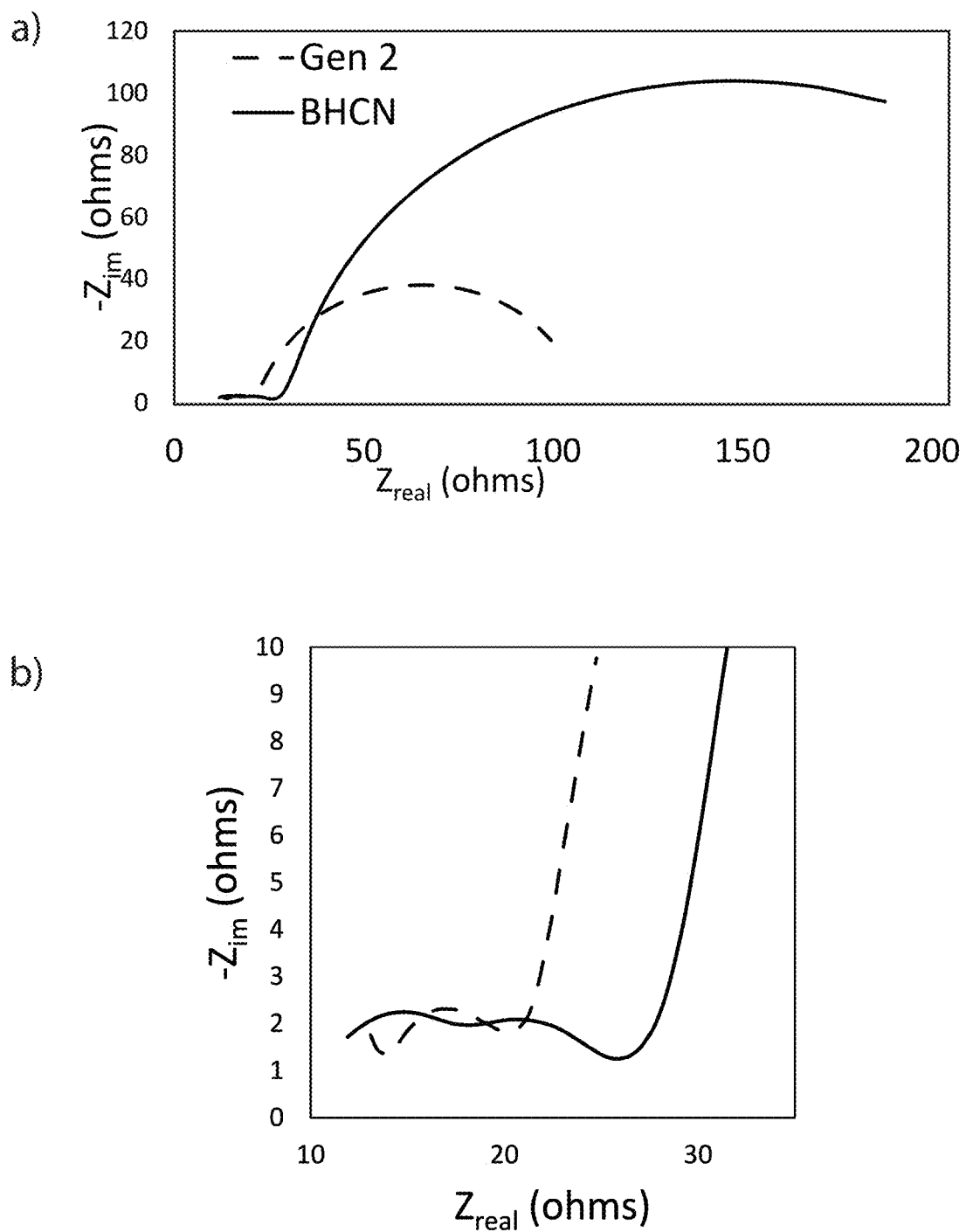
FIG. 7 illustrates electrochemical impedance spectroscopy (EIS) data for full coin cell lithium-ion batteries containing a Gen2 electrolyte solution and coin cell lithium-ion batteries containing an electrolyte solution containing BHCN, according to some aspects of the present disclosure.

FIG. 6 illustrates data showing the discharge capacity compared to voltage for lithium-ion batteries with an electrolyte solution containing BHCN and lithium-ion batteries using a Gen2 electrolyte, according to some aspects of the present disclosure. Full coin cells were fabricated using NMC 532 and graphite anodes in an argon filled glovebox (with water with less than about 0.1 ppm). Gen2 electrolytes were used as reference electrolytes and about 30 wt % BHCN was added to Gen2 for the BHCN sample. Cells were cycled at C10 during formation and C1 post formation, 3 C for the 50th cycle and 6 C for the 100th cycle. Although the cells containing 30 wt % BHCN performed modestly well some additional optimization is required. There is the same 0.1 V drop between the 1 C and 6 C initial discharge voltage which suggests that BHCN does not increase the reduction of $Ni^{3+}$ in the NMC 532 cathode. There is an increase in diffusivity for electrolytes containing BHCN it may be seen in FIG. 6 that the discharge is lower than expected. The decrease in capacity for the higher discharge rates can be explained by the higher cell impedance for cells containing approximately 30 wt % BHCN as shown in FIG. 7. A higher electrolyte resistance can be seen in the BHCN cells at the high frequency end of the electrochemical impedance spectroscopy (EIS) data, as shown in FIG. 7.

FIG. 7 illustrates EIS data for full coin cells containing an electrolyte solution containing BHCN, according to some aspects of the present disclosure. A modest increase can also be seen for the solid electrolyte interface (SEI) resistance, but a significant difference is seen in the intercalation resistance for the BHCN cells. This suggests the BHCN plays a part in the forming of a novel SEI layer yet to be optimized. In FIG. 7, the cells contain either a Gen 2 electrolyte or an electrolyte solution with about 30 wt % BHCN. Cells with BHCN show increased electrolyte electrode resistance. The high frequency range of the stand shows increase electrolyte resistance.

Figure 8:
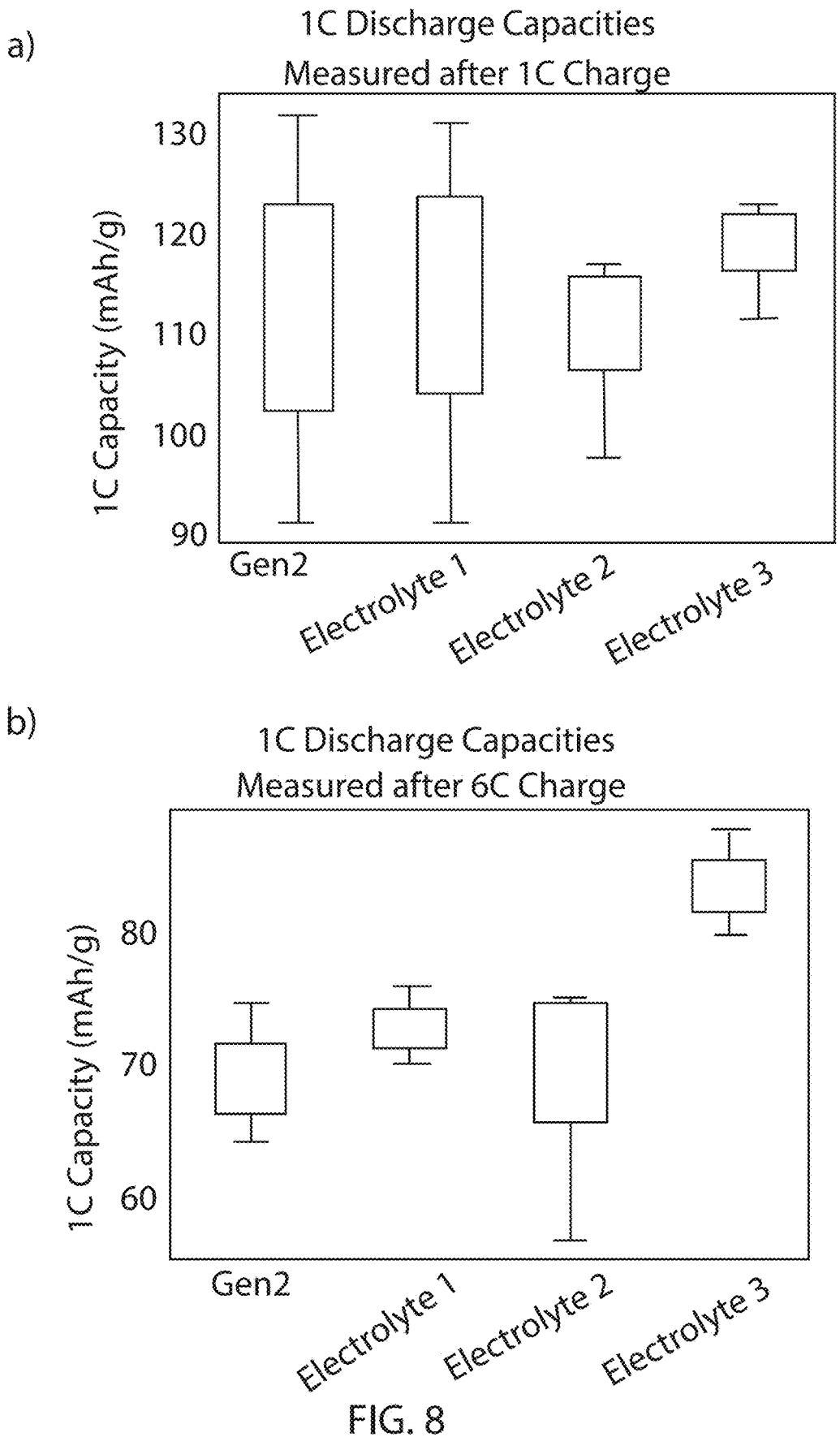
FIG. 8 illustrates discharge capacities for lithium-ion batteries containing a Gen2 electrolyte solution and lithium-ion batteries containing an electrolyte solution of about 10 wt % BHCN (referred to as "Electrolyte 1"), about 10 wt % BHCN and about 2 wt % fluoroethylene carbonate (FEC) (referred to as "Electrolyte 2"), and about 10 wt % BHCN, about 1 wt % FEC, and about 1 wt % vinylene carbonate (VC) (referred to as "Electrolyte 3"), according to some aspects of the present disclosure.

FIG. 8 illustrates discharge capacities for lithium-ion batteries containing a Gen2 electrolyte and lithium-ion batteries containing about 10 wt % BHCN (referred to as "Electrolyte 1"), about 10 wt % BHCN and about 2 wt % fluoroethylene carbonate (FEC) (referred to as "Electrolyte 2") and about 10 wt % BHCN, about 1 wt % FEC, and about 1 wt % vinylene carbonate (VC) (referred to as "Electrolyte 3"), according to some aspects of the present disclosure. Panel a) shows the 1 C discharge capacities measured after 1 C charge and panel b) shows the 1 C discharge capacities after 6 C charge. Both panel a) and panel b) were for cells having a maximum voltage of approximately 4.1 V. As shown in FIG. 8, the capacity of lithium-ion batteries containing an electrolyte solution having BHCN, either alone or in combination with FEC and/or VC (i.e., Electrolyte 1, Electrolyte 2, or Electrolyte 3), is greater than the capacity of lithium-ion batteries with a Gen2 electrolyte solution.

Figure 9:
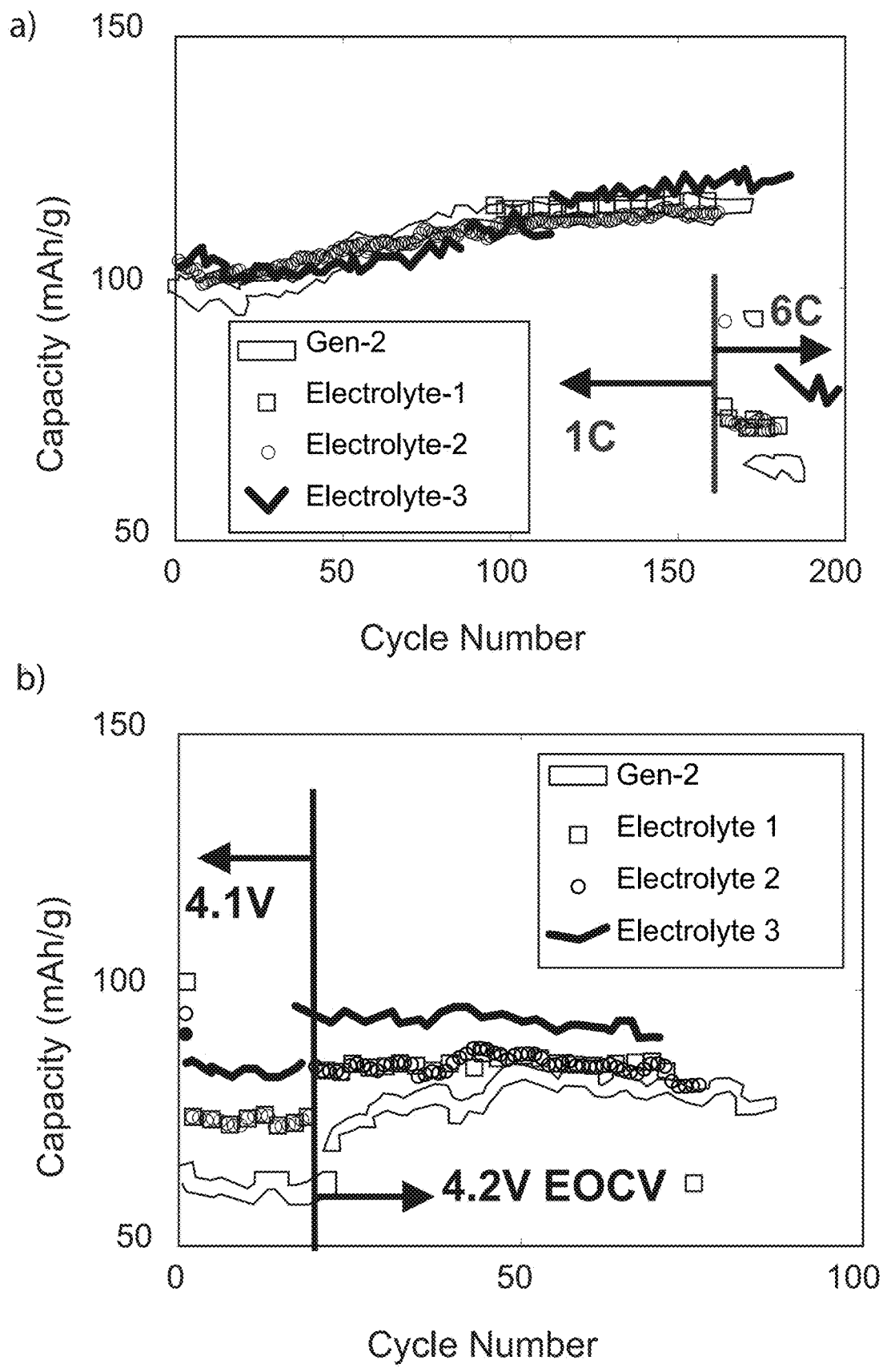
FIG. 9 illustrates capacity over several cycles for a lithium-ion battery containing a Gen2 electrolyte solution, Electrolyte 1, Electrolyte 2, and Electrolyte 3, according to some aspects of the present disclosure.

FIG. 9 illustrates capacity over several cycles for a lithium-ion battery containing a Gen2 electrolyte, Electrolyte 1, Electrolyte 2, and Electrolyte 3, according to some aspects of the present disclosure. Panel a) shows data for coin cells with round 2 electrodes. For both panel a) and panel b), the samples were kept at constant current (CC) and constant voltage (CV) with a time limit determined by the C rate. The current cut off for the CV step was set to approximately 10%, but not reached within the set time limit. As shown in FIG. 9, all formulations were stable for an approximately 4.2V full lithium-ion battery cell. Electrolyte 3 retained approximately 70% of the 1 C capacity when charged at the 6 C rate at 4.1V and approximately 77% at about 4.2V.

Figure 10:
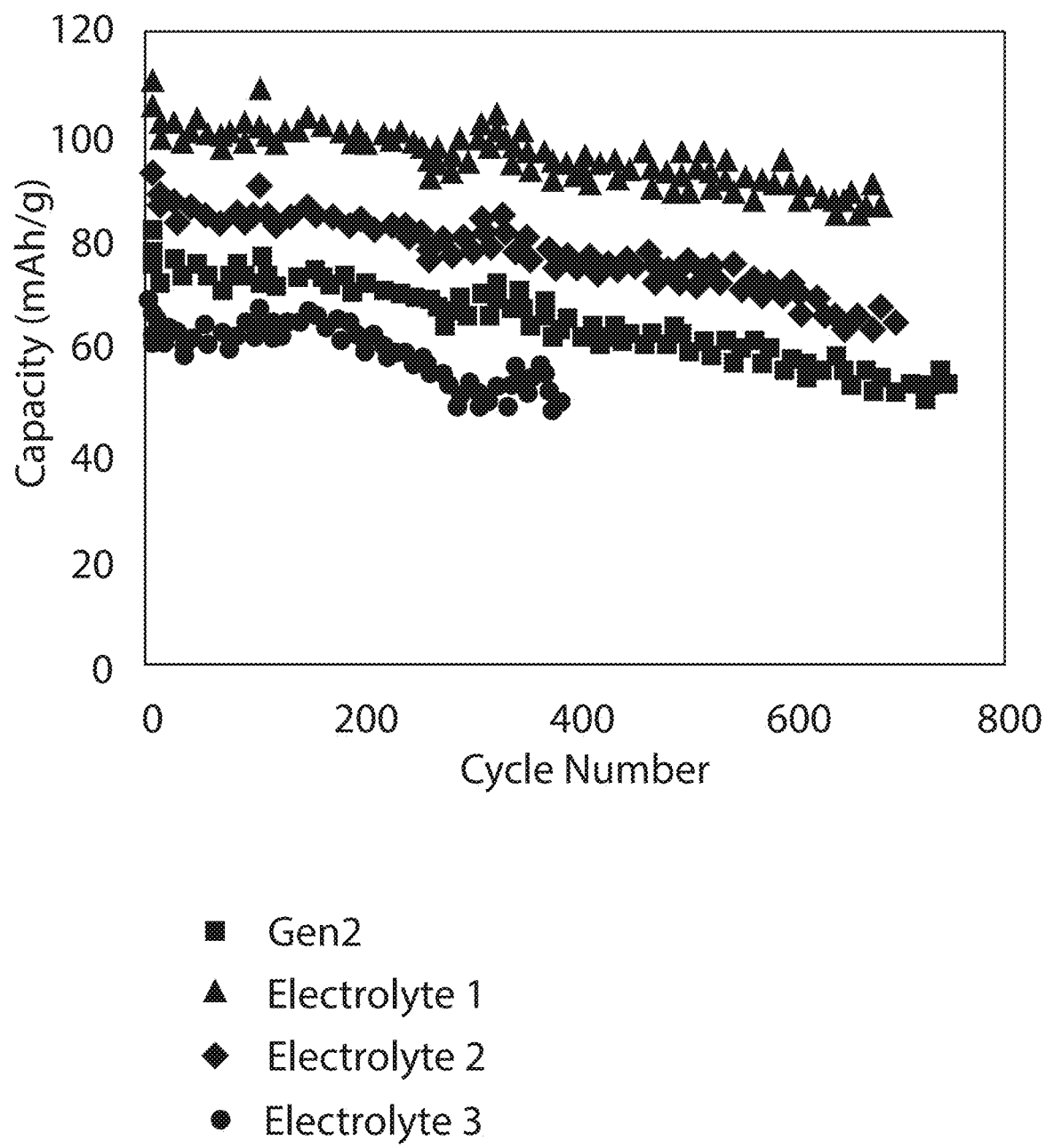
FIG. 10 illustrates capacity over a greater number of cycles for a lithium-ion battery containing a Gen2 electrolyte solution, Electrolyte 1, Electrolyte 2, and Electrolyte 3, according to some aspects of the present disclosure.

FIG. 10 illustrates capacity over a greater number of cycles for a lithium-ion battery containing a Gen2 electrolyte, Electrolyte 1, Electrolyte 2, and Electrolyte 3, according to some aspects of the present disclosure. As shown in FIG. 10, with larger cumulative cycles, the cells with an electrolyte solution containing BHCN (with or without FEC and/or VC) showed slightly higher capacity retention (i.e., lower fade). The results for electrolyte solutions containing BHCN with VC varied with concentration and cell format. The lithium-ion batteries used a three layer monoporous membrane (polypropylene (PP)/polyethylene (PE)/PP) having a thickness of approximately 20 μm as a separator.

Figure 11:
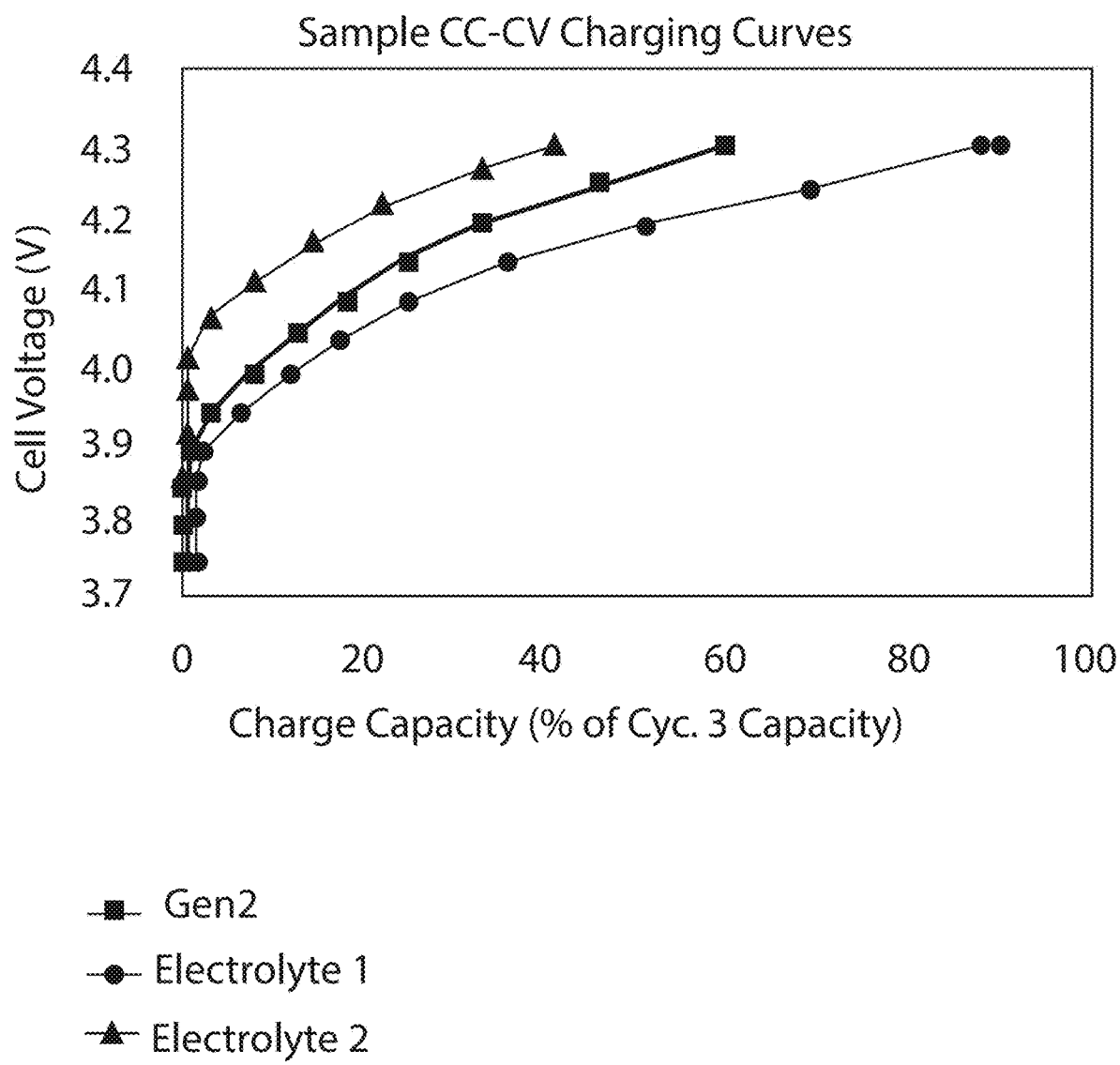
FIG. 11 illustrates cell voltage compared to charge capacity for a lithium-ion battery containing a Gen2 electrolyte solution, Electrolyte 1, and Electrolyte 2, according to some aspects of the present disclosure.

FIG. 11 illustrates cell voltage compared to charge capacity for a lithium-ion battery containing a Gen2 electrolyte, Electrolyte 1, and Electrolyte 2, according to some aspects of the present disclosure. The data shown in FIG. 11 was taken after about 100 cycles for samples held at CC-CV.

Figure 12:
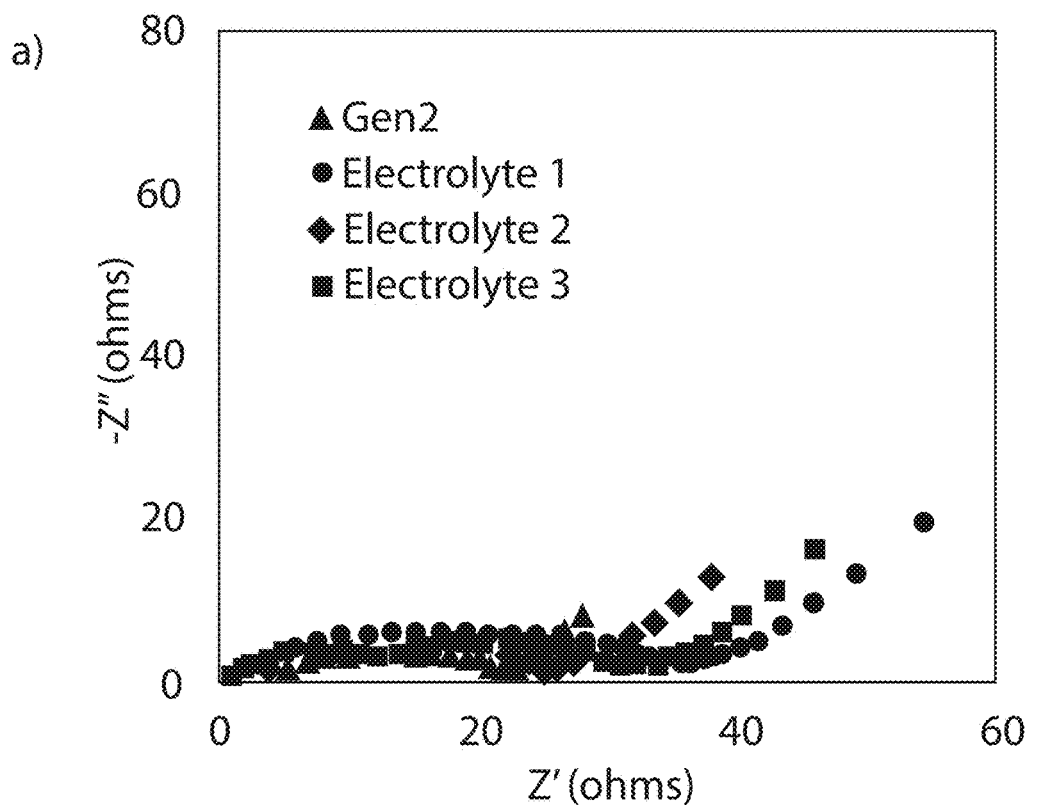
FIG. 12 illustrates EIS data for a lithium-ion battery containing a Gen2 electrolyte solution, Electrolyte 1, Electrolyte 2, and Electrolyte 3, according to some aspects of the present disclosure.
Figure 12:
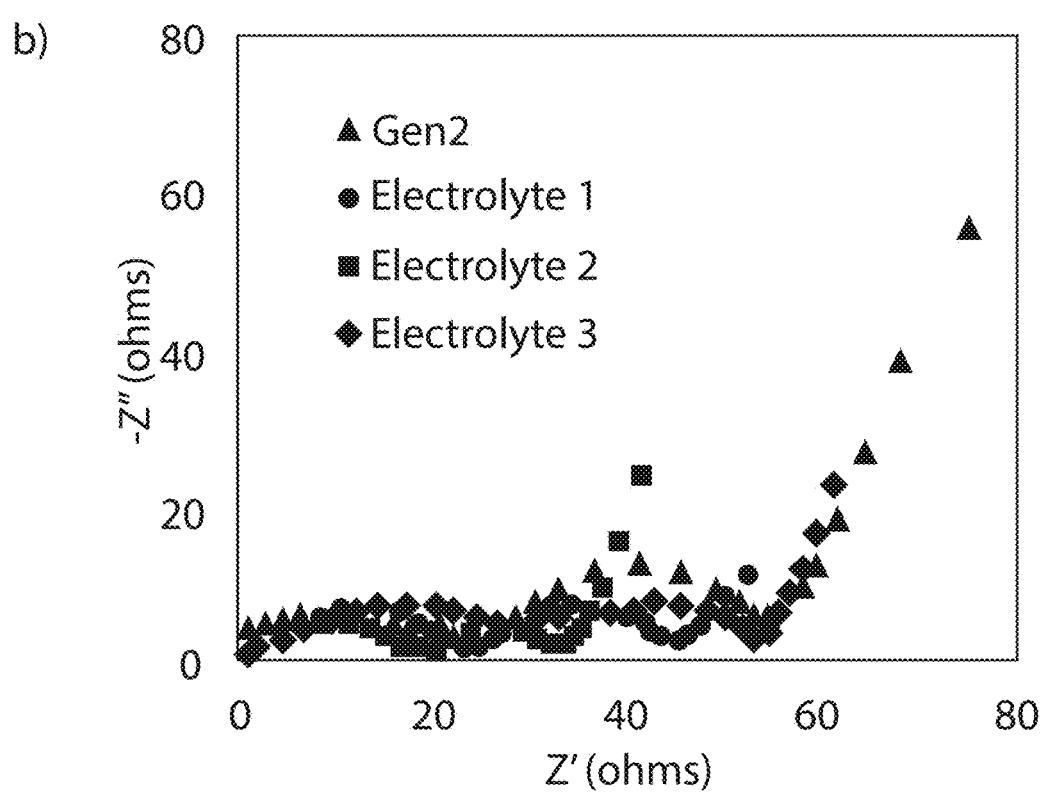

FIG. 12 illustrates EIS data for a lithium-ion battery containing a Gen2 electrolyte, Electrolyte 1, Electrolyte 2, and Electrolyte 3, according to some aspects of the present disclosure. As shown in both panel a) and panel b) of FIG. 12, lithium-ion batteries containing a Gen2 electrolyte start out with lower impedance; however, after about 1000 cycles, the impedance rise is lower for electrolyte solutions containing BHCN.

Figure 13:
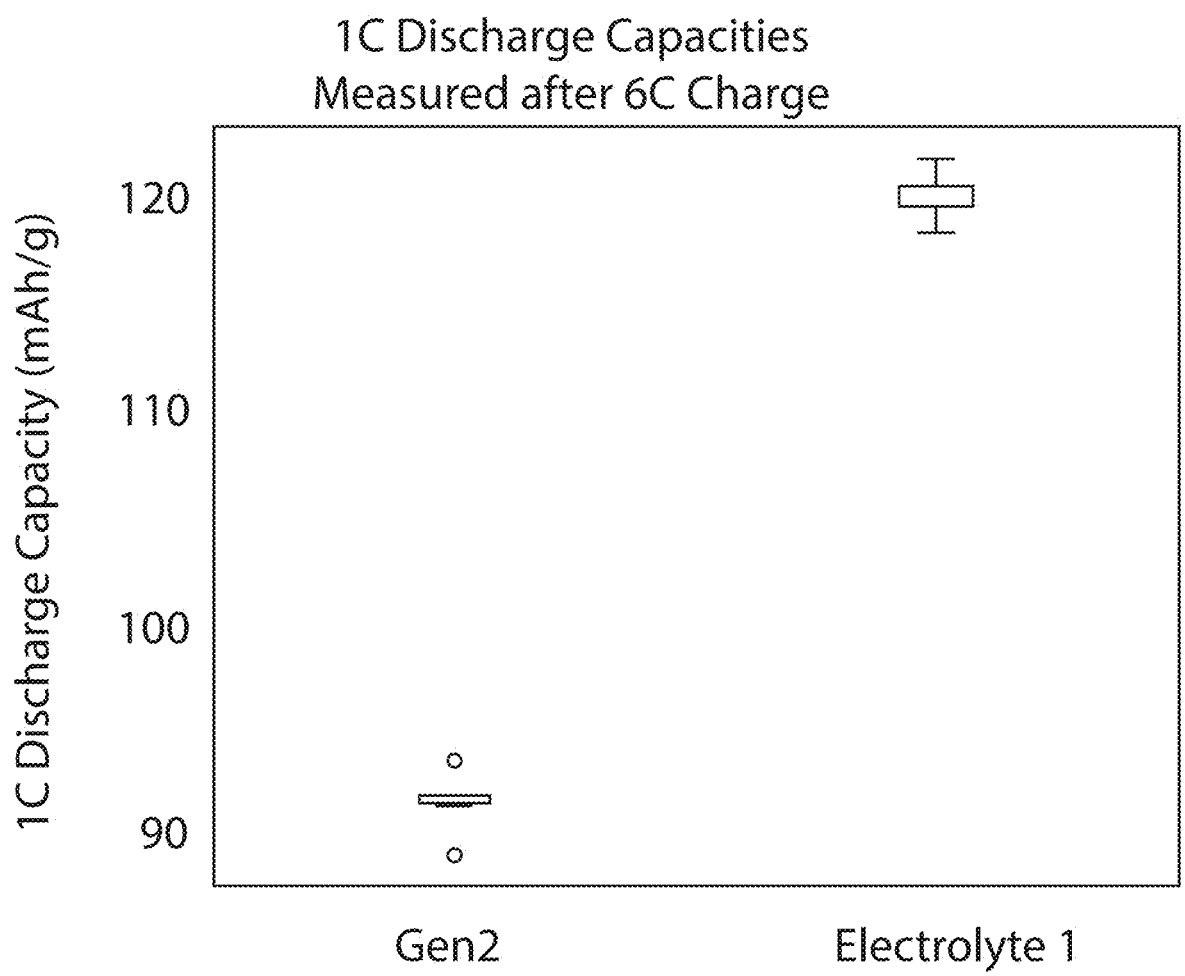
FIG. 13 illustrates discharge capacities for a lithium-ion battery containing a Gen2 electrolyte solution and Electrolyte 1, according to some aspects of the present disclosure.

FIG. 13 illustrates discharge capacities for a lithium-ion battery containing a Gen2 electrolyte and Electrolyte 1, according to some aspects of the present disclosure. Both lithium-ion batteries used a microporous monolayer membrane (PP) having a thickness of approximately 25 µm as a separator. The use of this separator appears to have increased the cell capacities by approximately 10-15%.

EXAMPLES

Example 1. A composition of an electrolyte solution for a lithium-ion battery, the composition comprising:
a fused bicyclic compound comprising:
an oxygen group in a cross bridge, and
a halide group.
Example 2. The composition of Example 1, wherein the fused bicyclic compound is 7-oxabicyclo[2.2.1]heptane-2-carbonitrile (BHCN).
Example 3. The composition of Example 2, wherein:
the BHCN has a concentration of about 5 wt % to about 50 wt %.
Example 4. The composition of any of Example 1-3, further comprising:
fluoroethylene carbonate (FEC).
Example 5. The composition of Example 4, wherein:
the FEC has a concentration of about 0.5 wt % to about 10 wt %.
Example 6. The composition of any of Examples 1-5, further comprising:
vinylene carbonate (VC).
Example 7. The composition of Example 6, wherein:
the VC has a concentration of about 0.5 wt % to about 10 wt %.
Example 8. The composition of any of Examples 2-7, wherein:
the BHCN has a concentration of about 10 wt %,
the FEC has a concentration of about 1 wt %, and
the VC has a concentration of about 1 wt %.
Example 9. The composition of any of Examples 1-8, further comprising:
a salt.
Example 10. The composition of Example 9, wherein the salt comprises at least one of lithium tetrafluoroborate ($LiBF_4$), lithium bis(trifluoromethanesulfonyl)imide (LiTFSI), lithium bis(oxalato)borate (LiBOB), lithium oxalyldifluoroborate (LiODFB), lithium fluoroalkylphosphate, lithium 4,5-dicycano-2-(trifluoromethyl)imidazolide (LiTDI), or lithium hexafluorophosphate ($LiPF_6$).
Example 11. The composition of Examples 9 or 10, wherein:
the salt has a concentration in the range of about 0.01 M to about 4.2 M.
Example 12. The composition of any of Examples 1-11, further comprising:
a cyclic ring compound and a linear chain solvent.
Example 13. The composition of Example 12, wherein:
the cyclic ring compound is less than about 30% of the weight of the electrolyte solution.
Example 14. The composition of Examples 12 or 13, wherein:
the linear chain solvent is in the range of about 10% to about 90% of the weight of the electrolyte solution.
Example 15. The composition of any of Examples 6-8, wherein:
the linear chain solvent is functionalized with at least one electron donating group.
Example 16. The composition of Example 15, wherein:
the electron donating group comprises at least one of a halide, a nitrile, or a nitrosyl.
Example 17. The composition of any of Examples 12-16, wherein:
the cyclic ring compound is ethylene carbonate, and
the linear chain solvent is ethyl methyl carbonate.
Example 18. The composition of any of Examples 1-17, wherein:
the lithium-ion battery has an increased cell capacity (mAh/g) over a typical lithium-ion battery containing 1.2M $LiPF_6$ in a combination of solvents (e.g., EC:EMC in the ratio 3:7) when the charging time to 4.2V is less than about 12 minutes.
Example 19. The composition of Example 18, wherein:
the increased cell capacity is at least 10%. when subjected to charging at currents of less than about 5 C in less than about 12 minutes for voltages less than about 4.2 V.
Example 20. The composition of any of Examples 1-19, wherein:
the lithium-ion battery can be charged from 1 to 100% state of charge in less than about 12 minutes.
Example 21. A lithium-ion battery comprising:
an anode;
a cathode; and
an electrolyte solution; wherein:
the electrolyte solution comprises:
a fused bicyclic compound comprising:
an oxygen group in a cross bridge, and
a halide group.
Example 22. The lithium-ion battery of Example 21, wherein:
the fused bicyclic compound is 7-oxabicyclo[2.2.1]heptane-2-carbonitrile (BHCN).
Example 23. The lithium-ion battery of Example 22, wherein:
the BHCN has a concentration of about 5 wt % to about 50 wt %.
Example 24. The lithium-ion battery of any of Example 21-23, further comprising:
fluoroethylene carbonate (FEC).
Example 25. The lithium-ion battery of Example 24, wherein:
the FEC has a concentration of about 0.5 wt % to about 10 wt %.
Example 26. The lithium-ion battery of any of Examples 21-25, further comprising:
vinylene carbonate (VC).
Example 27. The lithium-ion battery of Example 26, wherein:
the VC has a concentration of about 0.5 wt % to about 10 wt %.
Example 28. The lithium-ion battery of any of Examples 22-27, wherein:
the BHCN has a concentration of about 10 wt %,
the FEC has a concentration of about 1 wt %, and
the VC has a concentration of about 1 wt %.
Example 29. The lithium-ion battery of any of Examples 21-28, wherein:
the electrolyte solution further comprises a salt.
Example 30. The lithium-ion battery of Example 29, wherein:
the salt comprises at least one of lithium tetrafluoroborate ($LiBF_4$), lithium bis(trifluoromethanesulfonyl)imide (LiTFSI), lithium bis(oxalato)borate (LiBOB), lithium oxalyldifluoroborate (LiODFB), lithium fluoroalkylphosphate, lithium 4,5-dicycano-2-(trifluoromethyl)imidazolide (LiTDI), or lithium hexafluorophosphate (LiPF$_6$).

Example 31. The lithium-ion battery of Examples 29 or 30, wherein:
the salt has a concentration in the range of about 0.01 M to about 4.2 M.

Example 32. The lithium-ion battery of any of Examples 21-31, further comprising:
a cyclic ring compound and a linear chain solvent.

Example 33. The lithium-ion battery of Example 32, wherein:
the cyclic ring compound is less than about 30% of the weight of the electrolyte solution.

Example 34. The lithium-ion battery of Examples 32 or 33, wherein:
the linear chain solvent is in the range of about 10% to about 90% of the weight of the electrolyte solution.

Example 35. The lithium-ion battery of any of Examples 32-35, wherein:
the linear chain solvent is functionalized with at least one electron donating group.

Example 36. The lithium-ion battery of Example 35, wherein:
the electron donating group comprises at least one of a halide, a nitrile, or a nitrosyl.

Example 37. The lithium-ion battery of any of Examples 32-36, wherein:
the cyclic ring compound is ethylene carbonate, and
the linear chain solvent is ethyl methyl carbonate.

Example 38. The lithium-ion battery of any of Examples 15-25, wherein:
the lithium-ion battery has an increased cell capacity (mAh/g) over a typical lithium-ion battery containing 1.2M LiPF$_6$ in a combination of solvents (e.g., EC:EMC in the ratio 3:7) when the charging time to 4.2V is less than about 12 minutes.

Example 39. The lithium-ion battery of Example 38, wherein:
the increased cell capacity is at least 10%. when subjected to charging at currents of less than about 5 C in less than about 12 minutes for voltages less than about 4.2 V.

Example 40. The lithium-ion battery of any of Examples 21-39, wherein:
the lithium-ion battery can be charged from 1 to 100% state of charge in less than about 12 minutes.

Example 41. The lithium-ion battery of any of Examples 21-40, wherein:
the anode comprises graphite.

Example 42. The lithium-ion battery of any of Examples 21-41, wherein:
the anode comprises lithium metal.

Example 43. The lithium-ion battery of any of Examples 21-42, wherein:
the cathode comprises a transition metal oxide.

Example 44. The lithium-ion battery of Example 43, wherein:
the transition metal oxide comprises at least one of lithium cobalt oxide, lithium nickel oxide, lithium manganese oxide, lithium (nickel-manganese-oxide)-oxide, lithium (nickel-manganese-oxide), lithium (nickel cobalt aluminum)-oxide, or lithium (nickel manganese-aluminum)-oxide.

Example 45. A method for improving the performance of a lithium-ion battery, the method comprising:
including a fused bicyclic compound in an electrolyte solution; wherein:
the lithium-ion battery comprises:
an anode;
a cathode; and
the electrolyte solution, and
the fused bicyclic compound comprises:
an oxygen group in a cross bridge, and
a halide group.

Example 46. The method of Example 45, wherein:
the fused bicyclic compound is 7-oxabicyclo[2.2.1]heptane-2-carbonitrile (BHCN).

Example 47. The method of Example 46, wherein:
the BHCN has a concentration of about 5 wt % to about 50 wt %.

Example 48. The method of any of Examples 44-46, further comprising:
fluoroethylene carbonate (FEC).

Example 49. The method of Example 48, wherein:
the FEC has a concentration of about 0.5 wt % to about 10 wt %.

Example 50. The composition of any of Examples 45-49, further comprising:
vinylene carbonate (VC).

Example 51. The method of Example 50, wherein:
the VC has a concentration of about 0.5 wt % to about 10 wt %.

Example 52. The method of any of Examples 45-51, wherein:
the BHCN has a concentration of about 10 wt %,
the FEC has a concentration of about 1 wt %, and
the VC has a concentration of about 1 wt %.

Example 53. The method of any of Examples 45-52, wherein:
the electrolyte solution further comprises:
a salt.

Example 54. The method of Example 53, wherein:
the salt comprises at least one of lithium tetrafluoroborate (LiBF$_4$), lithium bis(trifluoromethanesulfonyl)imide (LiTFSI), lithium bis(oxalato)borate (LiBOB), lithium oxalyldifluoroborate (LiODFB), lithium fluoroalkylphosphate, lithium 4,5-dicycano-2-(trifluoromethyl)imidazolide (LiTDI), or lithium hexafluorophosphate (LiPF$_6$).

Example 55. The method of Examples 53 or 54, wherein:
the salt has a concentration in the range of about 0.01 M to about 4.2 M.

Example 56. The method of any of Examples 45-55, wherein:
the electrolyte solution further comprises:
a cyclic ring compound and a linear chain solvent.

Example 57. The method of Example 56, wherein:
the cyclic ring compound is less than about 30% of the weight of the electrolyte solution.

Example 58. The method of Examples 56 or 57, wherein:
the linear chain solvent is in the range of about 10% to about 90% of the weight of the electrolyte solution.

Example 59. The method of any of Examples 45-58, wherein:
the linear chain solvent is functionalized with at least one electron donating group.

Example 60. The method of Example 59, wherein:
the electron donating group comprises at least one of a halide, a nitrile, or a nitrosyl.

Example 61. The method of any of Examples 45-60, wherein:
the cyclic ring compound is ethylene carbonate, and
the linear chain solvent is ethyl methyl carbonate.

Example 62. The method of any of Examples 45-61, wherein:
the lithium-ion battery has an increased cell capacity (mAh/g) over a typical lithium-ion battery containing 1.2M $LiPF_6$ in a combination of solvents (e.g., EC:EMC in the ratio 3:7) when the charging time to 4.2V is less than about 12 minutes.

Example 63. The method of Example 62, wherein:
the increased cell capacity is at least 10%. when subjected to charging at currents of less than about 5 C in less than about 12 minutes for voltages less than about 4.2 V.

Example 64. The method of any of Examples 45-63, wherein:
the lithium-ion battery can be charged from 1 to 100% state of charge in less than about 12 minutes.

Example 65. The method of any of Examples 45-63, wherein:
the anode comprises graphite.

Example 66. The method of any of Examples 45-64, wherein:
the anode comprises lithium metal.

Example 67. The method of any of Examples 45-65, wherein:
the cathode comprises a transition metal oxide.

Example 68. The method of Example 67, wherein:
the transition metal oxide comprises at least one of lithium cobalt oxide, lithium nickel oxide, lithium manganese oxide, lithium (nickel-manganese-oxide)-oxide, lithium (nickel-manganese-oxide), lithium (nickel cobalt aluminum)-oxide, or lithium (nickel manganese-aluminum)-oxide.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods, and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms a (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. For example, when a device is set forth disclosing a range of materials, device components, and/or device configurations, the description is intended to include specific reference of each combination and/or variation corresponding to the disclosed range.

Every formulation or combination of components described or exemplified herein can be used to practice the invention, unless otherwise stated.

Whenever a range is given in the specification, for example, a density range, a number range, a temperature range, a time range, or a composition or concentration range, all intermediate ranges, and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter is claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

The invention claimed is:

1. A composition of an electrolyte solution for a lithium-ion battery, the composition comprising:
a fused bicyclic compound comprising: an oxygen group in a cross bridge;
a fluoroethylene carbonate (FEC); and
a salt; wherein:
the fused bicyclic compound comprises 7-oxabicyclo[2.2.1]heptane-2-carbonitrile BHCN)
the fused bicyclic compound has a concentration of about 5 wt % to about 50 wt %, and
the FEC has a concentration of about 0.5 wt % to about 10 wt %.

2. The composition of claim 1, wherein the salt comprises at least one of lithium tetrafluoroborate (LiBF$_4$), lithium bis(trifluoromethanesylfonyl)imide (LiTFSI), lithium oxalyldifluoroborate (LiODFB), lithium fluoroalkylphosphate, lithium 4,5-dicycano-2-(trifluoromethyl)imidazolide (LiTDI), or lithium hexafluoraphosphate (LiPF$_6$).

3. The composition of claim 1, wherein:
the salt has a concentration in the range of about 0.01 M to about 4.2 M.

4. The composition of claim 1, further comprising:
a vinylene carbonate (VC).

5. The composition of claim 4, wherein:
the VC has a concentration of about 0.5 wt % to about 10 wt %.

6. The composition of claim 4, wherein:
the fused bicyclic compound has a concentration of about 10 wt %,
the FEC has a concentration of about 1 wt %, and
the VC has a concentration of about 1 wt %.

7. A lithium-ion battery comprising:
an anode;
a cathode; and
an electrolyte solution; wherein:
the electrolyte solution comprises:
a fused bicyclic compound comprising an oxygen group in a cross bridge,
a fluoroethylene carbonate (FEC), and
a salt, wherein:
the fused bicyclic compound comprises 7-oxabicyclo [2.2.1]heptane-2-carbonitrile (BHCN),
the fused bicyclic compound has a concentration of about 5 wt % to about 50 wt %, and
the FEC has a concentration of about 0.5 wt % to about 10 wt %.

8. The lithium-ion battery of claim 7, wherein:
the lithium-ion battery has an increased cell capacity (mAh/g) over a typical lithium-ion battery containing 1.2M LiPF$_6$ in a combination of solvents (e.g., EC:EMC in the ratio 3:7) when the charging time to 4.2V is less than about 12 minutes.

9. The lithium-ion battery of claim 8, wherein:
the increased cell capacity is at least 10%, when subjected to charging at currents of less than about 5 C in less than about 12 minutes for voltages less than about 4.2 V.

10. The lithium-ion battery of claim 7, wherein:
the lithium-ion battery can be charged from 1 to 100% state of charge in less than about 12 minutes.

11. The lithium-ion battery of claim 7, further comprising:
a vinylene carbonate (VC).

12. The lithium-ion battery of claim 11, wherein:
the VC has a concentration of about 0.5 wt % to about 10 wt %.

13. The lithium-ion battery of claim 11, wherein:
the fused bicyclic compound has a concentration of about 10 wt %,
the FEC has a concentration of about 1 wt %, and
the VC has a concentration of about 1 wt %.

* * * * *